(12) United States Patent
Lapinski et al.

(10) Patent No.: US 9,302,959 B2
(45) Date of Patent: Apr. 5, 2016

(54) PROCESS FOR INCREASING THE YIELD OF AN ISOMERIZATION ZONE

(71) Applicant: UOP LLC, Des Plaines, IL (US)

(72) Inventors: Mark P. Lapinski, Aurora, IL (US); Matthew Lippmann, Chicago, IL (US); Gregory Funk, Carol Stream, IL (US)

(73) Assignee: UOP LLC, Des Plaines, IL (US)

( * ) Notice: Subject to any disclaimer, the term of this patent is extended or adjusted under 35 U.S.C. 154(b) by 215 days.

(21) Appl. No.: 14/267,838

(22) Filed: May 1, 2014

(65) Prior Publication Data

US 2015/0315101 A1    Nov. 5, 2015

(51) Int. Cl.
*C07C 5/27*    (2006.01)
*C07C 7/00*    (2006.01)

(52) U.S. Cl.
CPC .. *C07C 7/005* (2013.01); *C07C 5/27* (2013.01)

(58) Field of Classification Search
CPC ........................................................ C07C 5/27
USPC ........................................ 585/737, 738, 748
See application file for complete search history.

(56) References Cited

U.S. PATENT DOCUMENTS

| | | | |
|---|---|---|---|
| 3,136,825 A | 6/1964 | Ryan et al. | |
| 3,617,516 A * | 11/1971 | Van Gooswilligen | ... B01J 27/06 208/134 |
| 3,812,199 A | 5/1974 | Chen et al. | |
| 3,953,537 A | 4/1976 | Chloupek et al. | |
| 4,191,845 A | 3/1980 | Rubin et al. | |
| 5,026,951 A | 6/1991 | Schmidt et al. | |
| 5,396,016 A | 3/1995 | Jablonski et al. | |
| 5,489,727 A | 2/1996 | Randolph et al. | |
| 6,423,880 B1 | 7/2002 | Randolph et al. | |
| 7,053,261 B2 | 5/2006 | Herbst et al. | |
| 7,067,448 B1 | 6/2006 | Weitkamp et al. | |
| 7,485,768 B1 | 2/2009 | Rice et al. | |
| 7,902,418 B2 | 3/2011 | Schmidt et al. | |
| 2005/0101814 A1 | 5/2005 | Foley et al. | |
| 2012/0074039 A1 | 3/2012 | Gonzalez et al. | |
| 2012/0184794 A1 | 7/2012 | Shecterle | |

FOREIGN PATENT DOCUMENTS

NL    8800685 A    10/1989

OTHER PUBLICATIONS

Rezgui et al., "Pentane isomerization and disproportionation catalyzed by sulfated zirconia promoted with iron and manganese," Catalysis Letters (1996), v. 37(1-2), pp. 5-8.
Maness, Jr. et al. "Paraffin isomerization and disproportionation catalyzed by Pd-loaded fluorided mordenites," Journal of Catalysis (1989), v. 117(2), pp. 322-334.

(Continued)

*Primary Examiner* — Thuan D Dang

(57) ABSTRACT

A process for increasing a yield of an isomerization zone by removing at least a portion of the $C_6$ cyclic hydrocarbons from a stream having $iC_4$ hydrocarbons, $iC_5$ hydrocarbons, and $iC_6$ hydrocarbons prior to the stream being passed into the same isomerization zone. Suppression of the $iC_4$ hydrocarbons does not occur, allowing the $iC_4$ hydrocarbons to be isomerized in the same isomerization zone as the $iC_5$ hydrocarbons and $iC_6$ hydrocarbons.

17 Claims, 1 Drawing Sheet

(56) References Cited

OTHER PUBLICATIONS

Juszczyk et al., "Neopentane conversion over Pd/γ—Al2O3," Catalysis Letters (1995), v. 31(1), pp. 37-45.

Karpinski et al., "Reaction of Neopentane with Hydrogen over Pd, Pt, Ir and Rh," Journal of the Chemical Society, Faraday Transactions (1987), v. 83(4), pp. 1293-1305.

* cited by examiner

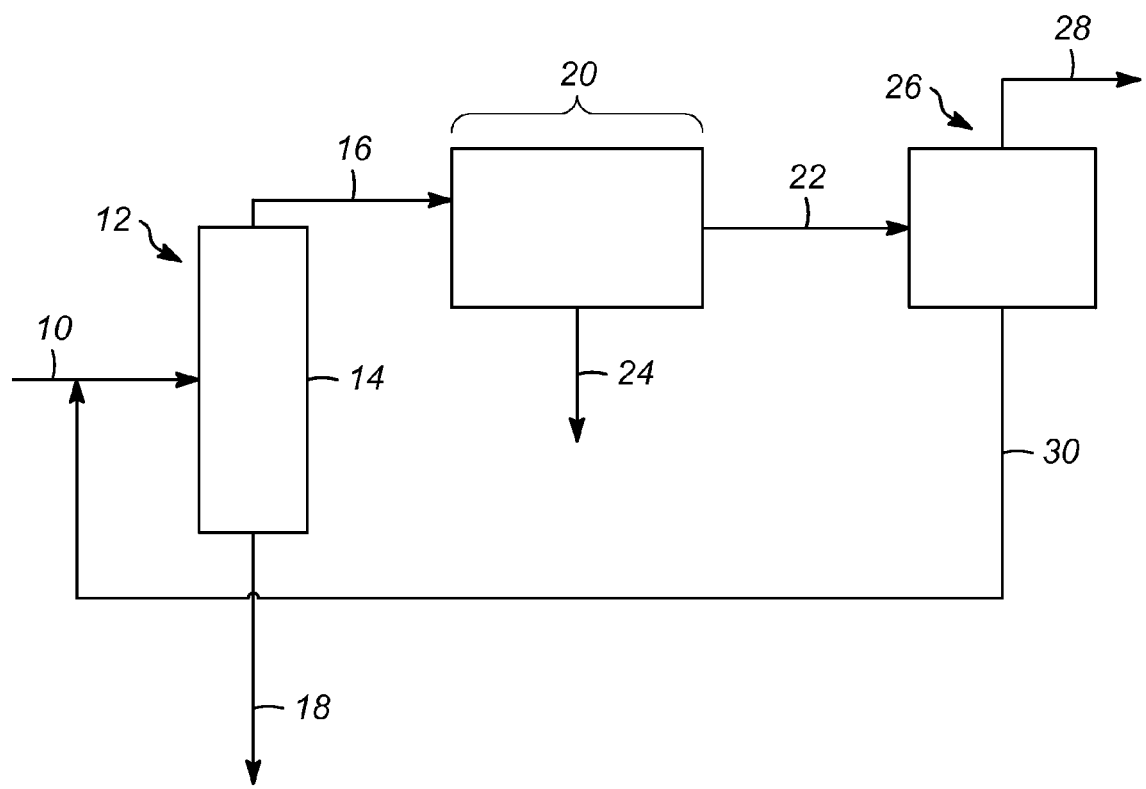

PROCESS FOR INCREASING THE YIELD OF AN ISOMERIZATION ZONE

FIELD OF THE INVENTION

This invention relates to processes for separating out various fractions of a naphtha stream to increase the yields of normal paraffins in an isomerization zone.

BACKGROUND OF THE INVENTION

Ethylene and propylene are important chemicals for use in the production of other useful materials, such as polyethylene and polypropylene. Polyethylene and polypropylene are two of the most common plastics found in use today and have a wide variety of uses for, for example, a material for fabrication and as a material for packaging. Other uses for ethylene and propylene include the production of vinyl chloride, ethylene oxide, ethylbenzene and alcohol.

The great bulk of the ethylene consumed in the production of the plastics and petrochemicals such as polyethylene is produced by the thermal cracking of higher molecular weight hydrocarbons. Steam is usually mixed with the feed stream to the cracking reactor to reduce the hydrocarbon partial pressure and enhance olefin yield and to reduce the formation and deposition of carbonaceous material in the cracking reactors. The process is therefore often referred to a steam cracking or pyrolysis.

The composition of the feed to the steam cracking reactor affects the results. A fundamental basis of this is the propensity of some hydrocarbons to crack more easily than others. The normal ranking of tendency of the hydrocarbons to crack to ethylene is normally given as: normal paraffins; iso-paraffins; olefins; naphthenes; and, aromatics. Benzene and other aromatics are particularly resistant to steam cracking and undesirable as cracking feed stocks, with only the alkyl side chains being cracked to produce the desired product.

The feed stream to a steam cracking unit can be quite diverse and can be chosen from a variety of petroleum fractions. The feed stream to the subject process preferably has a boiling point range falling within the naphtha boiling point range or about 36 to 205° C. It is preferred that the feed stream does not contain appreciable amounts, e.g. more than 5 mole %, of $C_{12}$ hydrocarbons. A representative feed stream to the subject process is a $C_5$-$C_{11}$ fraction produced by fractional distillation of a hydrotreated petroleum fraction. Hydrotreating is desired to reduce the sulfur and nitrogen content of the feed down to acceptable levels. A second representative feed is a similar fraction comprising $C_5$ through $C_9$ hydrocarbons.

The feed to a steam cracking unit is also normally a mixture of hydrocarbons varying both by type of hydrocarbon and carbon number. This variety results in it being very difficult to separate less desirable feed components, such as naphthenes and aromatics, from the feed stream by fractional distillation. The hydrocarbons that are not the normal paraffins can be removed by solvent extraction or adsorption. These hydrocarbons can be upgraded to improve the feedstock to the steam cracking unit.

One way to upgrade these hydrocarbons is to pass the non-normal paraffins to an isomerization zone. In the isomerization zone, the non-normal paraffins are converted, in the presence of a catalyst, into normal paraffins.

Based upon current designs, conversion of $iC_5$ hydrocarbons and $iC_6$ hydrocarbons to normal paraffins in an isomerization zone is limited, by equilibrium conditions, to about 25% and 13% per pass, respectively. Based upon typical processing conditions, full conversion of the iso-paraffins entails large recycle streams, large fractionation columns, and large utility costs. The per pass conversion rates can be increased for example, by increasing the temperature of the isomerization zone, by lowering the liquid hourly space velocities (LHSV), or both, which leads to the cracking of some of the paraffins to lighter $C_4$– hydrocarbons. The cracking reactions can lead to the production of undesired low-value methane.

Furthermore, it has been observed that, within the isomerization zone, the $C_4$ hydrocarbon isomerization activity is suppressed by $C_5+$ hydrocarbon concentrations greater than about 3.0 wt %, and $C_6+$ hydrocarbon concentrations greater than about 0.1 wt %, and $C_7+$ hydrocarbon concentrations greater than about 0.001 wt %. Thus, $C_4$ hydrocarbon isomerization is conducted in a separate process and is not combined with the isomerization of $C_5$ and $C_6$ light naphtha streams.

It would be desirable to have an isomerization process that allows for $iC_4$, $iC_5$, and $iC_6$ hydrocarbons to be efficiently and effectively converted to normal paraffins in the same isomerization zone.

SUMMARY OF THE INVENTION

It has been discovered that $iC_4$, $iC_5$, and $iC_6$ hydrocarbons can be processed together under conditions for isomerization without suppression of the isomerization of the $iC_4$ hydrocarbons by removing $C_6+$ cyclic hydrocarbons from the $C_4$ to $C_6$ feed stream in order to promote disproportionation reactions and higher overall conversions per pass.

Accordingly, in a first embodiment of the invention a process for increasing a yield of an isomerization zone is provided in which includes: separating a portion of $C_6$ cyclic hydrocarbons from a naphtha stream comprising $C_4+$ hydrocarbons to provide a $C_6$ cyclic hydrocarbons lean stream; separating $iC_4$ hydrocarbons, $iC_5$ hydrocarbons, and $iC_6$ hydrocarbons from the $C_6$ cyclic hydrocarbons lean stream; and, passing at least one stream being rich in $iC_4$ hydrocarbons, $iC_5$ hydrocarbons, $iC_6$ hydrocarbons, or a combination thereof to an isomerization zone.

The process may also include separating an effluent from the isomerization zone into an overhead stream comprising $C_3$– hydrocarbons and a bottoms stream comprising $C_4+$ hydrocarbons. The bottoms stream comprising $C_4+$ hydrocarbons may be combined with at least a portion of the naphtha stream.

It is contemplated that the process includes controlling an amount of $C_6$ cyclic hydrocarbons passed into the isomerization zone. The amount of $C_6$ cyclic hydrocarbons passed into the isomerization zone may be controlled by selectively adding a stream of $C_6$ cyclic hydrocarbons to the isomerization zone. Additionally, it is contemplated that controlling an operating parameter of a separation zone used to separate the $C_6$ cyclic hydrocarbons from the naphtha stream.

It is further contemplated that the process includes passing the naphtha stream to a first separation zone and separating the naphtha stream in the first separation zone into an overhead stream and a bottoms stream. The overhead stream is the $C_6$ cyclic hydrocarbons lean stream and the bottoms stream is rich in n-hexane and $C_6$ cyclic hydrocarbons. The overhead stream may be passed from the first separation zone to a second separation zone and separated in the second separation zone into the at least one stream that is rich in $iC_4$ hydrocarbons, $iC_5$ hydrocarbons, $iC_6$ hydrocarbons, or a combination thereof.

In some embodiments of the present invention, the second separation zone comprises at least three separator columns. The overhead stream from the first separation zone may be separated in a first separator column of the second separation zone into an overhead stream, an intermediate stream, a bottoms stream. The overhead stream from the first separator column of the second separation zone may be rich in $C_4+$ hydrocarbons, and, the intermediate stream of the first separator column of the second separation zone may be rich in $iC_6$ hydrocarbons. The bottoms stream from the isomerization zone may be recycled to the first column from the second separation zone. Additionally, the bottoms streams from the first separator column and the second separator column may be combined.

In some embodiments of the present invention, the second separation zone comprises at least one adsorption zone. The overhead stream from the first separation zone may be separated in the at least one absorption zone into a first stream and a second stream. The first stream is rich in $iC_4$ hydrocarbons, $iC_5$ hydrocarbons, $iC_6$ hydrocarbons, or a combination thereof. The second stream is rich in n-butane, n-pentane, and n-hexane. It is further contemplated that the bottoms stream from the isomerization zone is recycled to the first separation zone, the second separation zone, or both.

In another embodiment of the present invention, the invention provides a process for increasing a yield of an isomerization zone which includes: removing $C_6$ cyclic hydrocarbons from at least one stream comprising $iC_4$ hydrocarbons, $iC_5$ hydrocarbons, $iC_6$ hydrocarbons, or combinations thereof, to provide a $C_6$ cyclic hydrocarbons lean stream; and, passing the $C_6$ cyclic hydrocarbons lean stream an isomerization zone.

The process may also include separating n-butane, n-pentane, and n-hexane from the $C_6$ cyclic hydrocarbons lean stream prior to passing the $C_6$ cyclic hydrocarbons lean stream in to the isomerization zone. The $C_6$ cyclic hydrocarbons may be separated in a first separation zone. The normal paraffins, n-butane, n-pentane, and n-hexane, may be separated in a second separation zone having at least three separation columns. In some embodiments, n-butane, n-pentane, and n-hexane are separated in an adsorption zone.

Additional embodiments and details of the present invention are set forth in the following detailed description of the invention.

DETAILED DESCRIPTION OF THE DRAWINGS

The drawing is a simplified process diagram in which the FIGURE shows a process flow diagram of a process according to one embodiment of the present invention.

DETAILED DESCRIPTION OF THE INVENTION

As mentioned above, it has been discovered that the efficient conversion of $iC_4$, $iC_5$, and $iC_6$ hydrocarbons to normal paraffins in the isomerization zone can be achieved by removing at least a portion of the $C_6$ cyclic hydrocarbons, such as cyclohexane, methyl-cyclopentane, and benzene, from the stream passed into the isomerization zone.

The ability to combine the isomerization of the $C_4$, $C_5$, and $C_6$ hydrocarbons will lead to lower capital expenditures and lower operating expenses because the two separate isomerization zones can be combined. Thus, such a process allows for less equipment, as well as more efficient use of the remaining equipment.

As shown in the FIGURE, in an exemplary embodiment of the present invention, a feed stream 10 is passed into a first separation zone 12. The feed stream 10 is preferably hydrotreated naphtha comprising $C_4+$ hydrocarbons (meaning hydrocarbons having four or more carbon atoms).

The first separation zone 12 may include a separator column 14, such as a fractionation column. As will be appreciated, the depiction of column 14 is simplified as all the auxiliary operational components, such as controls, trays, condenser and reboiler, may be of conventional design. In other embodiments, the feed stream 10, or multiple feed streams, can be fed into the column 14 at different locations if appropriate. The column 14 will typically contain conventional vapor-liquid contacting equipment such as trays or packing. The type of tray and design details such as tray type, tray spacing and layout may vary within the column 14.

The column 14 will separate the feed stream 10 into an overhead stream 16 and a bottoms stream 18. The overhead stream 16 may comprise $C_4$, $C_5$ and $iC_6$ hydrocarbons. Since at least a portion of the $C_6$ cyclic hydrocarbons have been removed from the portion of the feed stream 10 in the overhead stream 16, the overhead stream 16 will be a $C_6$ cyclic hydrocarbons lean stream. The bottoms stream 18 may comprise n-hexane, $C_6$ cyclic hydrocarbons, and $C_7+$ hydrocarbons. Furthermore, depending on the operating conditions of the column 14, the bottoms stream 18 may also contain some small amounts of iC6 hydrocarbons, such as 3-methylpentane. The bottoms stream 18 may be passed to various other zones, such as, for example: to saturation and then to a steam cracker; to a reformer and then to an aromatic complex; to saturation, then to a ring operating reactor, and then to a steam cracker; or a combination of the foregoing. The further processing of the bottoms stream 18 is not necessary for the understanding and practicing of the present invention.

Returning to the FIGURE, the overhead stream 16 from the first separation zone 12 may be passed to a second separation zone 20. The second separation zone may comprise for example, an adsorption zone.

Such an adsorption zone can include, as is known, a single large bed of adsorbent or in several parallel beds on a swing bed basis. However, it has been found that simulated moving bed adsorptive separation provides several advantages such as high purity and recovery. Therefore, many commercial scale petrochemical separations especially for the recovery of mixed paraffins are performed using simulated countercurrent moving bed (SMB) technology. Further details on equipment and techniques for operating an SMB process may be found in U.S. Pat. Nos. 3,208,833; 3,214,247; 3,392,113; 3,455,815; 3,523,762; 3,617,504; 4,006,197; 4,133,842; and 4,434,051, all of which are incorporated by reference in their entirety. A different type of simulated moving bed operation which can be performed using similar equipment, adsorbent and conditions but which simulates co-current flow of the adsorbent and liquid in the adsorption chambers is described in U.S. Pat. Nos. 4,402,832 and 4,498,991, which are incorporated by reference in their entirety.

Operating conditions for the adsorption chamber used in the subject invention include, in general, a temperature range of from about 20° C. to about 250° C. Adsorption conditions also preferably include a pressure sufficient to maintain the process fluids in liquid phase; which may be from about atmospheric to about 600 psig. Desorption conditions generally include the same temperatures and pressure as used for adsorption conditions. It is generally preferred that an SMB process is operated with an A:F flow rate through the adsorption zone in the broad range of about 1:1 to 5:0.5 where A is the volume rate of "circulation" of selective pore volume and F is the feed flow rate. The practice of the subject invention requires no significant variation in operating conditions or desorbent composition within the adsorbent chambers. That is, the adsorbent preferably remains at the same temperature throughout the process during both adsorption and desorption.

The adsorbent used in the first adsorption zone preferably comprises aluminosilicate molecular sieves having relatively uniform pore diameters of about 5 angstroms. This is provided by commercially available type 5A molecular sieves produced by UOP LLC.

A second adsorbent which could be used in the adsorption zone comprises silicalite. Silicalite is well described in the literature. It is disclosed and claimed in U.S. Pat. No. 4,061,724 issued to Grose et al., which is incorporated by reference in its entirety. A more detailed description is found in the article, "Silicalite, A New Hydrophobic Crystalline Silica Molecular Sieve," Nature, Vol. 271, Feb. 9, 1978 which is incorporated herein by reference for its description and characterization of silicalite. Silicalite is a hydrophobic crystalline silica molecular sieve having intersecting bent-orthogonal channels formed with two cross-sectional geometries, 6 Å and 5.1-5.7 Å elliptical on the major axis. This gives silicalite great selectivity as a size selective molecular sieve. Due to its aluminum free structure composed of silicon dioxide, silicalite does not show ion-exchange behavior. Silicalite is also described in U.S. Pat. Nos. 5,262,144; 5,276,246 and 5,292,900, which are incorporated by reference in their entirety. These basically relate to treatments which reduce the catalytic activity of silicalite to allow its use as an adsorbent.

The active component of the adsorbent is normally used in the form of particle agglomerates having high physical strength and attrition resistance. The agglomerates contain the active adsorptive material dispersed in an amorphous, inorganic matrix or binder, having channels and cavities therein which enable fluid to access the adsorptive material. Methods for forming the crystalline powders into such agglomerates include the addition of an inorganic binder, generally a clay comprising a silicon dioxide and aluminum oxide, to a high purity adsorbent powder in a wet mixture. The binder aids in forming or agglomerating the crystalline particles. The blended clay-adsorbent mixture may be extruded into cylindrical pellets or formed into beads which are subsequently calcined in order to convert the clay to an amorphous binder of considerable mechanical strength. The adsorbent may also be bound into irregular shaped particles formed by spray drying or crushing of larger masses followed by size screening. The adsorbent particles may thus be in the form of extrudates, tablets, spheres or granules having a desired particle range, preferably from about 16 to about 60 mesh (Standard U.S. Mesh) (1.9 mm to 250 microns). Clays of the kaolin type, water permeable organic polymers or silica are generally used as binders.

The active molecular sieve component of the adsorbent will preferably be in the form of small crystals present in the adsorbent particles in amounts ranging from about 75 to about 98-wt. % of the particle based on volatile-free composition. Volatile-free compositions are generally determined at 900° C., after the adsorbent has been calcined, in order to drive off all volatile matter. The remainder of the adsorbent will generally be the inorganic matrix of the binder present in intimate mixture with the small particles of the silicalite material. This matrix material may be an adjunct of the manufacturing process for the silicalite, for example, from the intentionally incomplete purification of the silicalite during its manufacture.

Those skilled in the art will appreciate that the performance of an adsorbent is often greatly influenced by a number of factors not related to its composition such as operating conditions, feed stream composition and the water content of the adsorbent. The optimum adsorbent composition and operating conditions for the process are therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500° C. under an inert gas purge such as nitrogen for a period of time sufficient to achieve a constant weight. For the subject process it is preferred that the water content of the adsorbent results in an LOI at 900° C. of less than 7.0% and preferably within the range of from 0 to 4.0 wt. %.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

U.S. Pat. No. 4,992,618 issued to S. Kulprathipanja, and which is incorporated by reference in its entirety, describes the use of a "prepulse" of a desorbent component in an SMB process for recovering normal paraffins. The prepulse is intended to improve the recovery of the extract normal paraffins across the carbon number range of the feed. The prepulse enters the adsorbent chamber at a point before (downstream) the feed injection point. A related SMB processing technique is the use of "zone flush." The zone flush forms a buffer zone between the feed and extract bed lines to keep the desorbent from entering the adsorption zone. While the use of a zone flush requires a more complicated, and thus more costly rotary valve, the use of zone flush is preferred in the adsorption zones when high purity extract product are desired. In practice, a quantity of the mixed component desorbent recovered overhead from the extract and raffinate columns may be passed into a separate splitter column. A high purity stream of the lower strength component of the mixed component desorbent is recovered and used as the zone flush stream. Further information on the use of dual component desorbents and on techniques to improve product purity such as the use of flush streams may be obtained from U.S. Pat. Nos. 3,201,491; 3,274,099; 3,715,409; 4,006,197 and 4,036,745 which are incorporated herein by reference in their entirety for their teaching on these aspects of SMB technology.

It has become customary in the art to group the numerous beds in the SMB adsorption chamber(s) into a number of zones. Usually the process is described in terms of 4 or 5 zones. First contact between the feed stream and the adsorbent is made in Zone I, the adsorption zone. The adsorbent or stationary phase in Zone I becomes surrounded by liquid which contains the undesired isomer(s), that is, the raffinate. This liquid is removed from the adsorbent in Zone II, referred to as a purification zone. In the purification zone the undesired raffinate components are flushed from the void volume of the adsorbent bed by a material which is easily separated from the desired component by fractional distillation. In Zone III of the adsorbent chamber(s) the desired isomer is released from the adsorbent by exposing and flushing the adsorbent with the desorbent (mobile phase). The released desired isomer and accompanying desorbent are removed from the adsorbent in the form of the extract stream. Zone IV is a portion of the adsorbent located between Zones I and III which is used to segregate Zones I and III. In Zone IV desorbent is partially removed from the adsorbent by a flowing mixture of desorbent and undesired components of the feed stream. The liquid flow through Zone IV prevents contamination of Zone III by Zone I liquid by flow cocurrent to the simulated motion of the adsorbent from Zone III toward Zone I. A more thorough explanation of simulated moving bed processes is given in the Adsorptive Separation section of the Kirk-Othmer Encyclopedia of Chemical Technology at page 563. The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber.

In an SMB process the several steps e.g. adsorption and desorption, are being performed simultaneously in different parts of the mass of adsorbent retained in the adsorbent chamber(s) of the process. If the process was being performed with two or more adsorbent beds in a swing bed system then the steps may be performed in a somewhat interrupted basis, but adsorption and desorption will most likely occur at the same time.

Returning to the FIGURE, alternatively or additionally, the second separation zone 20 may also include a plurality of separation columns. These columns may be, for example, fractionation columns, similar in design to column 14 in the first separation zone 12. One of ordinary skill in the art would appreciate that a series of columns can be used to separate iso-paraffins from normal paraffins. For example, a deisohexanizer (DIH) column, a deisopentanizer (DIP) column and a deisobutanizer column (DIB) can be utilized to separate the types of hydrocarbons.

Whether the second separation zone 20 includes a plurality of separation columns, an adsorption zone, a combination thereof, or a different separation process, the second separation zone 20 will separate the iso-paraffins from the normal pentane, normal butane, and other non-iso-paraffins that may be in the $C_6$ cyclic hydrocarbons lean stream 16.

The second separation zone 20 provides at least one stream 22 that is rich in $iC_4$ hydrocarbons, $iC_5$ hydrocarbons, $iC_6$ hydrocarbons, or any combination thereof. In other words, although the FIGURE depicts a single stream 22, it is contemplated that multiple streams rich in iso-paraffins are produced by the second separation zone 20. For example, one stream rich in $iC_4$ hydrocarbons, a stream rich in $iC_5$ hydrocarbons, and one stream rich in $iC_6$ hydrocarbons may each be provided by the second separation zone 20.

The second separation zone 20 will also provide at least one stream 24 being rich in normal pentane, normal butane, normal hexane and other non-iso-paraffins. As will be discussed below, some of the normal paraffins are the products from the isomerization reactions. Again, although this stream 24 is depicted as a single stream, it is contemplated that multiple streams are provided. This stream 24, being rich in normal paraffins, may be sent to, for example, a stream cracker for the production of light olefins.

The stream 22 which is rich in iso-paraffins is passed to an isomerization zone 26. Again it is recognized that this can be multiple streams. In the isomerization zone 26, the $iC_4$, $iC_5$, and $iC_6$ hydrocarbons, in the presence of hydrogen and an isomerization catalyst, are converted into normal paraffins. The isomerization zone 26, as is known, typically contains a series of reactors and a separation column.

While it is known that cracking of some of the paraffins can occur in an isomerization zone 26 to form $C_4$- hydrocarbons, it has been discovered that the conversion of $iC_5$ and $iC_6$ hydrocarbons increases significantly via disproportionation reactions due to the fact that the stream 22 passed into the isomerization zone 26 is lean in $C_6$ cyclic hydrocarbons. It is believed that the disproportionation reactions occur by the combination of two iso-paraffin hydrocarbons followed by scission into one lighter hydrocarbon and one heavier hydrocarbon. For example, two $iC_5$ hydrocarbons can combine and form an $iC_4$ hydrocarbon and an $iC_6$ hydrocarbon in the presence of hydrogen. The $iC_4$ hydrocarbons can react via disproportionation to form a $C_3$ hydrocarbon and an $iC_5$ hydrocarbon. The $iC_4$ hydrocarbons also convert to $nC_4$ hydrocarbons via isomerization reactions in the isomerization zone. A key characteristic of the present invention is the production of $C_3$ and $C_4$ normal paraffins via disproportionation and isomerization reactions with low production of low-value undesired methane as a cracked product.

Further, it has been discovered that $iC_4$, $iC_5$, and $iC_6$ hydrocarbons can be processed together under conditions for isomerization without suppression of the isomerization of the $iC_4$ hydrocarbons by removing $C_6$+ cyclic hydrocarbons from the $C_4$ to $C_6$ feed stream in order to promote disproportionation reactions and higher overall conversions per pass.

The disproportionation reactions are enabled by the use of an isomerization catalyst, and the isomerization zone 26 can include, chlorided alumina, sulfated zirconia, tungstated zirconia or zeolite-containing isomerization catalysts. The isomerization catalyst may be amorphous, e.g. based upon amorphous alumina, or zeolitic. A zeolitic catalyst would still normally contain an amorphous binder. The catalyst may comprise a sulfated zirconia and platinum as described in U.S. Pat. No. 5,036,035 and European patent application 0 666 109 A1 or a platinum group metal on chlorided alumina as described in U.S. Pat. No. 5,705,730 and U.S. Pat. No. 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component. These documents are incorporated herein for their teaching as to catalyst compositions, isomerization operating conditions and techniques. Notwithstanding the foregoing, if the effluent is to be passed to a steam cracker, it is contemplated that the catalyst in the isomerization zone 26 is a non-chlorided catalyst. By using such a catalyst, there is no need to scrub the effluent to reduce the amount of chloride form the catalyst passes to the steam cracker.

Contacting within the isomerization zone 26 may be effected using the catalyst in a fixed-bed system, a moving-bed system, a fluidized-bed system, or in a batch-type operation. The reactants may be contacted with the bed of catalyst particles in upward, downward, or radial-flow fashion. The reactants may be in the liquid phase, a mixed liquid-vapor phase, or a vapor phase when contacted with the catalyst particles, with a mixed phase or vapor phase being preferred. The isomerization zone may be in a single reactor or in two or more separate reactors with suitable means therebetween to insure that the desired isomerization temperature is maintained at the entrance to each zone. Two or more reactors in sequence enable improved isomerization through control of individual reactor temperatures and for partial catalyst replacement without a process shutdown.

Isomerization conditions in the isomerization zone 26 include reactor temperatures usually ranging from about 40° C. to 250° C. Reactor operating pressures generally range from about 100 kPa to 10 MPa absolute, preferably between about 0.5 and 4 MPa absolute. Liquid hourly space velocities range from about 0.2 to about 25 volumes of isomerizable hydrocarbon feed per hour per volume of catalyst.

Hydrogen is admixed with or remains with the isomerization feed to the isomerization zone to provide a mole ratio of hydrogen to hydrocarbon feed of from about 0.01 to 20. The hydrogen may be supplied totally from outside the process or supplemented by hydrogen recycled to the feed after separation from isomerization reactor effluent. Light hydrocarbons and small amounts of inerts such as nitrogen and argon may be present in the hydrogen. Water should be removed from hydrogen supplied from outside the process, preferably by an adsorption system as is known in the art.

Over a range of LHSV (1 to 5 $hr^{-1}$) for a feed stream which is lean in $C_6$+ cyclic hydrocarbons in the presence of a chlorided-alumina isomerization catalyst, more favorable ratios of the yield of normal paraffins, which include ethane, propane, $nC_4$, $nC_5$ and $nC_6$ hydrocarbons, to the yield of methane are obtained by regulating the outlet hydrogen to hydrocarbon feed mole ratio ($H_2$/HC) to less than 0.7, preferably, to less than about 0.2, while operating at average reactor temperatures greater then about 176.6° C. (350° F.), preferably greater than about 190.5° C. (375° F.). Similarly for other isomerization catalyst types, the temperatures and $H_2$/HC ratios can be set to obtain favorable ratios of desired normal paraffins to undesired methane.

Furthermore, it is contemplated that an amount of $C_6$ cyclic hydrocarbons passed to the isomerization zone is adjusted. This is believed to allow for control of at least the disproportionation reactions and the customization of the product streams. For example, an operating parameter of the various separation zones may be controlled so that an amount of $C_6$ cyclic hydrocarbons does reach the isomerization zone. Additionally, and alternatively, a $C_6$ cyclic hydrocarbons rich stream may be introduced into the steams passing into the isomerization zone.

Returning to the FIGURE, a first stream 28 recovered from the isomerization zone comprises $C_3$– hydrocarbons. This stream 28 may be sent to gas treatment, then to a steam cracker. The further processing of this stream 28 is not necessary for the understanding and practicing of the present invention.

A second stream 30 recovered from the isomerization zone 26 will comprise $C_4$+ hydrocarbons, including normal paraffins. This stream 30 may be recycled back through at least one of the first separation zone 12 and the second separation zone 20 to separate out the normal paraffins from the iso-paraffins.

Returning to the first separation zone 12, although not shown, it is also contemplated that a ring opening reactor is utilized on a stream having the $C_6$ cyclic hydrocarbons, for example, on the bottoms stream 18 or via a side cut stream of column 14 from the first separation zone 12. In the ring opening reactor zone, the cyclic hydrocarbons, in the presence of a catalyst, are converted into straight chain hydrocarbons. Typically, such reactions occur in a ring opening reactor. The products of the ring opening reactor which can include methane to $C_7$+ hydrocarbons are separated into, for example, a $C_3$– hydrocarbon stream, a $C_4$ to $C_6$ hydrocarbons stream, and a $C_6$ cyclic hydrocarbons and $C_7$+ hydrocarbons stream. The $C_6$ cyclic hydrocarbons and $C_7$+ hydrocarbons stream may be combined with the bottoms stream from the first separation zone. The $C_3$– hydrocarbon stream may be passed to further processing units or zones. The $C_4$ to $C_6$ hydrocarbons stream may be combined with the overhead stream 16 of the first separation zone 12, and passed to the second separation zone as discussed above.

In order to demonstrate that $iC_4$ hydrocarbons can isomerize in the presence of significant concentrations of $C_5$ and $C_6$ hydrocarbons but in the absence of $C_6$ cyclic hydrocarbons, a chlorided-alumina catalyst that contained platinum was loaded and operated under isomerization conditions of 3.1 MPa (450 psig), at a rate of 2 $h^{-1}$ LHSV, with an 0.1 outlet $H_2$/HC mole ratio, and with an average catalyst bed of 190.5° C. (375° F.). A feed stream was used which was rich in $C_5$ and $C_6$ hydrocarbons and contained trace amount of $C_4$ components and did not contain any $C_6$ cyclic hydrocarbons (see Table 1).

TABLE 1

|  | FEED | PRODUCT | MODEL |
|---|---|---|---|
| COMPONENTS (wt %) |  |  |  |
| $H_2$ |  | 0.3 |  |
| $C_1$ |  | 0.1 |  |
| $C_2$ |  | 0.2 |  |
| $C_3$ |  | 4.8 |  |
| $iC_4$ | 0.01 | 14.7 |  |
| $nC_4$ | 0.01 | 7.1 |  |
| $iC_5$ | 55.5 | 29.5 |  |
| $nC_5$ | 1.9 | 10.7 |  |
| $iC_6$ | 41.9 | 26.9 |  |
| $nC_6$ | 0.5 | 4.2 |  |
| Cyclopentane | 0.0 | 0.1 |  |
| $C_7$+ | 0.2 | 1.6 |  |
| SUM | 100.0 | 100.0 |  |
| RATIOS (%) |  |  |  |
| $nC_4/(nC_4+iC_4)$ | — | 32.5 | 31.0 |
| $nC_5/(nC_5+iC_5)$ | 3.2 | 26.6 | 26.6 |
| $nC_6/(nC_6+iC_6)$ | 1.1 | 13.4 | 13.5 |

While the feed did not contain appreciable concentrations of $C_4$ hydrocarbons, significant amounts of $iC_4$ hydrocarbons are produced mainly through disproportionation reactions and $nC_4$ hydrocarbons are produced mainly through isomerization reactions. Additionally, some lesser amounts of $C_4$ hydrocarbons may be produced through cracking reactions of heavier components.

Based upon the theoretical modeling performed at the same conditions as the experimental data, the iso-paraffins and normal paraffins are at, or very close to equilibrium for the $C_4$, $C_5$ and $C_6$ hydrocarbons as demonstrated by the close matching of the normal to iso- and normal ratios in Table 1 for the experimental results compared to the model predictions. The $C_4$ hydrocarbon equilibrium is achieved in the presence of $C_5$+ hydrocarbons concentrations of over 40 wt % which is significantly higher than the observed 3.0 wt % limit for $C_4$ isomerization processes. This demonstrates that feed steams containing $iC_4$ hydrocarbons passed into an isomerization zone in accordance with the present invention may isomerize and achieve or closely approach equilibrium to form $nC_4$ hydrocarbons under isomerization conditions.

Thus, it is contemplated that the $iC_4$, $iC_5$ and $iC_6$ hydrocarbons components can be processed together, surprisingly achieving or closely approaching isomerization equilibrium under conditions for isomerization and produce significant amounts of normal paraffins. Such a process can eliminate the need for a second downstream isomerization zone for the conversion of $iC_4$ hydrocarbons to $nC_4$ hydrocarbons.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understating the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for the isomerization of isoparaffins to normal paraffins, the process comprising:
   separating a portion of C6 cyclic hydrocarbons from a naphtha stream comprising C4+ hydrocarbons to provide a C6 cyclic hydrocarbons lean stream;
   separating iC4 paraffinic hydrocarbons, iC5 paraffinic hydrocarbons, and iC6 paraffinic hydrocarbons from the C6 cyclic hydrocarbons lean stream; and,
   passing in iC4 paraffinic hydrocarbons, iC5 paraffinic hydrocarbons, and iC6 paraffinic hydrocarbons to an isomerization zone containing a chlorided alumina catalyst to isomerize isoparaffins to normal paraffins, disproportionate at least some isoparaffins, and crack at least some isoparaffins; and
   controlling an amount of C6 cyclic hydrocarbons passed into the isomerization zone by at least one of the following:
   selectively adding a stream of C6 cyclic hydrocarbons to the isomerization zone; and,
   controlling an operating parameter of a separation zone used to separate the C6 cyclic hydrocarbons from the naphtha stream.

2. The process of claim 1 further comprising:
   separating an effluent from the isomerization zone into an overhead stream comprising C3− hydrocarbons and a bottoms stream comprising C4+ hydrocarbons.

3. The process of claim 2 further comprising:
   combining the bottoms stream comprising C4+ hydrocarbons with at least a portion of the naphtha stream.

4. The process of claim 1 further comprising:
   passing the naphtha stream to a first separation zone; and,
   separating the naphtha stream in the first separation zone into an overhead stream and a bottoms stream, the overhead stream being the C6 cyclic hydrocarbons lean stream and the bottoms stream being rich in n-hexane and C6 cyclic hydrocarbons.

5. The process of claim 4 further comprising:
   passing the overhead stream from the first separation zone to a second separation zone; and,
   separating the overhead stream from the first separation zone in the second separation zone into the at least one stream being rich in iC4 paraffinic hydrocarbons, iC5 paraffinic hydrocarbons, iC6 paraffinic hydrocarbons, or a combination thereof.

6. The process of claim 5 wherein the second separation zone comprises:
   at least three separator columns.

7. The process of claim 6 further comprising:
   separating the overhead stream from the first separation zone in a first separator column of the second separation zone into an overhead stream, an intermediate stream, a bottoms stream,
   the overhead stream from the first separator column of the second separation zone being rich in C4+ hydrocarbons, and,
   the intermediate stream of the first separator column of the second separation zone being rich in iC6 paraffinic hydrocarbons.

8. The process of claim 7 further comprising:
   recycling the bottoms stream from the isomerization zone to the first column from the second separation zone.

9. The process of claim 7 further comprising:
   combining the bottoms stream from the first separator column and the second separator column.

10. The process of claim 5 wherein the second separation zone comprises:
    at least one adsorption zone.

11. The process of claim 10 further comprising:
    separating the overhead stream from the first separation zone in the at least one absorption zone into a first stream and a second stream,
    the first stream being rich in iC4 paraffinic hydrocarbons, iC5 paraffinic hydrocarbons, iC6 paraffinic hydrocarbons, or a combination thereof, and,
    the second stream being rich in n-butane, n-pentane, and n-hexane.

12. The method of claim 11 further comprising:
    recycling the bottoms stream from the isomerization zone to the first separation zone.

13. The method of claim 11 further comprising:
    recycling the bottoms stream from the isomerization zone to the second separation zone.

14. The process of claim 1 further comprising:
    separating n-butane, n-pentane, and n-hexane from the C6 cyclic hydrocarbons lean stream prior to passing the C6 cyclic hydrocarbons lean stream into the isomerization zone.

15. The process of claim 14 wherein the C6 cyclic hydrocarbons are separated in a first separation zone.

16. The process of claim 15 wherein n-butane, n-pentane, and n-hexane are separated in a second separation zone having at least three separation columns.

17. The process of claim 15 wherein n-butane, n-pentane, and n-hexane are separated in a second separation zone having an adsorption zone.

* * * * *